US006986787B1

(12) United States Patent  (10) Patent No.: US 6,986,787 B1
Baker, Jr.  (45) Date of Patent: Jan. 17, 2006

(54) ACCOMODATIVE INTRAOCULAR LENS

(76) Inventor: David Littleton Baker, Jr., 2550 Adamsbrooke Dr., Conway, AR (US) 72034-4826

( * ) Notice: Subject to any disclaimer, the term of this patent is extended or adjusted under 35 U.S.C. 154(b) by 198 days.

(21) Appl. No.: 10/388,326

(22) Filed: Mar. 12, 2003

(51) Int. Cl.
A61F 2/16 (2006.01)
(52) U.S. Cl. .................... 623/6.37; 623/6.39; 623/6.43
(58) Field of Classification Search ............... 623/6.11, 623/6.18, 6.37–6.39, 6.4, 6.41–6.43, 6.45, 623/6.46, 6.51–6.55
See application file for complete search history.

(56) References Cited

U.S. PATENT DOCUMENTS

| 4,494,254 | A |   | 1/1985  | Lopez ............................. 3/13 |
| 4,790,847 | A | * | 12/1988 | Woods ....................... 623/6.37 |
| 4,842,600 | A |   | 6/1989  | Feaster ........................... 623/6 |
| 4,950,290 | A |   | 8/1990  | Kamerling ..................... 623/6 |
| 5,133,751 | A |   | 7/1992  | Bayers ........................... 623/6 |
| 5,653,752 | A |   | 8/1997  | Silvestrini et al. ............. 623/5 |
| 5,766,244 | A | * | 6/1998  | Binder ....................... 623/6.54 |
| 6,364,906 | B1 |  | 4/2002  | Baikoff et al. ............... 623/6.4 |
| 6,660,035 | B1 | * | 12/2003 | Lang et al. ................ 623/6.37 |
| 2003/0114927 | A1 | * | 6/2003 | Nagamoto ................. 623/6.37 |

FOREIGN PATENT DOCUMENTS

| EP | 337390 A2 | * | 10/1989 |
| FR | 2666504 A1 | * | 3/1992 |
| JP | 02126847 A | * | 5/1990 |

* cited by examiner

Primary Examiner—David H. Willse
Assistant Examiner—Javier G. Blanco
(74) Attorney, Agent, or Firm—Henry Law Firm; Mark Henry

(57) ABSTRACT

An accommodative intraocular lens is provided to replace a natural lens. The intraocular lens structure includes an optical portion and a haptic portion. The optical portion includes a replacement lens while the haptic portion includes the structure that holds the lens in position while keeping the anterior capsular sac taunt and annular in shape. The haptic in the present invention stabilizes the annular structure of the peripheral zone at the capsular sac's largest diameter and also stabilizes the conical structure of the capsular sac as well. The haptic structure includes a helical coil of increasing radius from the lens to the terminating annular ring that thus forms a conical coil spring. Compression and relaxation of the coiled (spring) haptics between the anterior and posterior capsule, during tightening and relaxation of lens zonule and ciliary body, move the lens to anteriorly and posteriorly and induces accommodation.

13 Claims, 5 Drawing Sheets

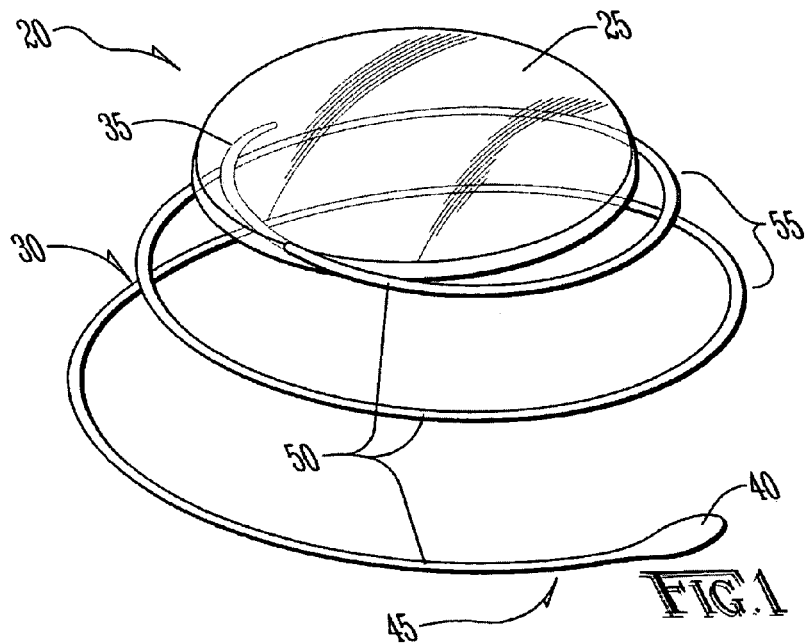
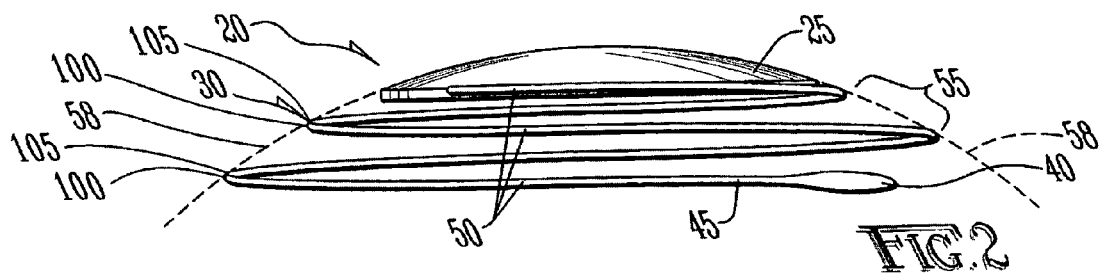

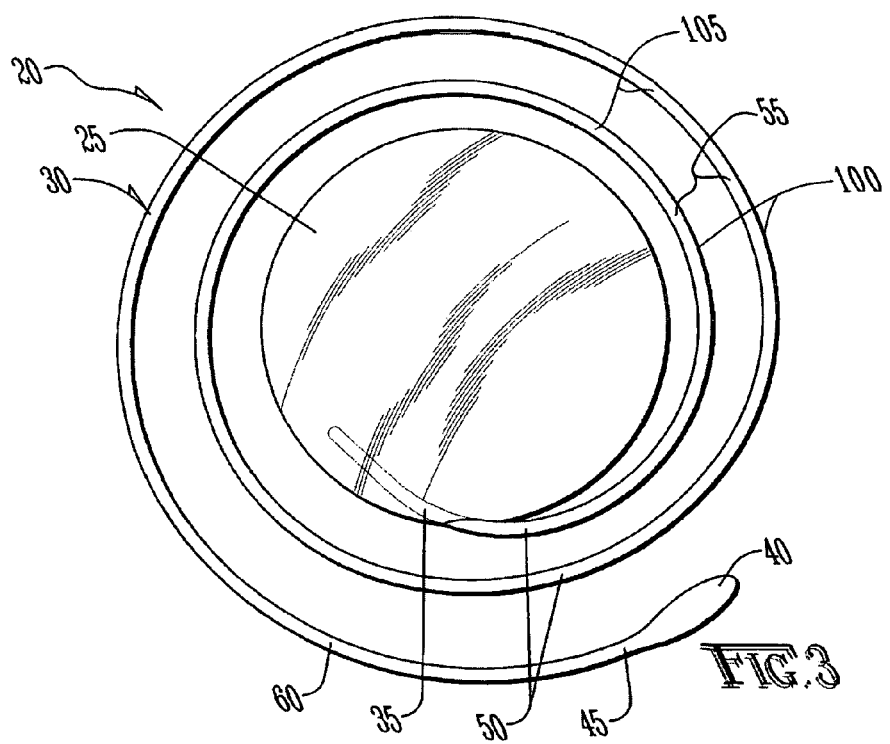
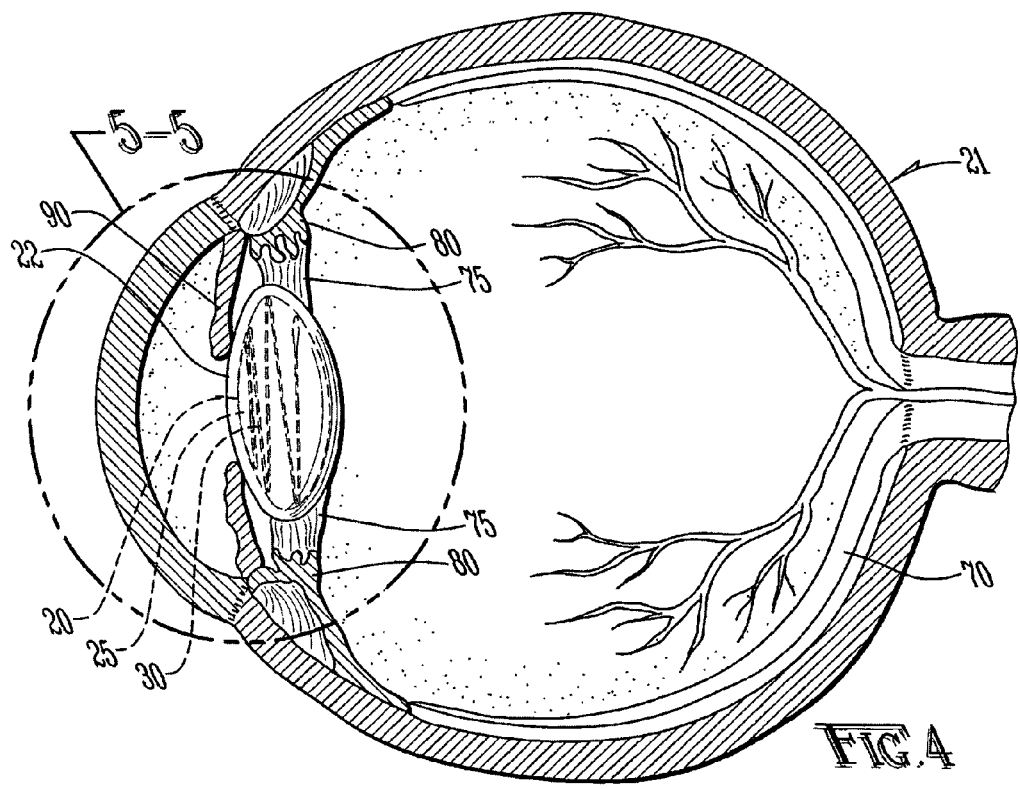

ACCOMODATIVE INTRAOCULAR LENS

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Field of the Invention

The present invention relates to the field of medical technology in general. In particular, the present invention relates specifically to an improved intraocular lens designed specifically such that the focal length between the lens and the retina can be varied in a manner similar to the manner the focal length of a natural lens varies. Known art may be found in U.S. Class 623, subclasses 5 and 6 as well as in other classes and subclasses.

2. Description of the Known Art

As will be appreciated by those skilled in the art, a replacement intraocular lens may be implanted to replace a natural lens for patients requiring such treatment as for example in cataract removal. These replacement surgeries have become more common recently as a preferential method for addressing certain ocular ailments. Details of a typical procedure are contained in U.S. Pat. No. 6,364,906 to Baikoff, the teachings of which are hereby expressly incorporated by reference.

A replacement intraocular lens consists of biocompatible material that may be characterized as having two sections. The first section is termed an optical part, which is the lens. The second section is termed a haptic part, which is the structure that holds the lens in position while keeping the anterior capsular bag taunt and annular in shape. Both these functions are important for proper vision to result from the replacement surgery.

The optical requirements for replacement lens have been well established. Most lens materials currently used also allow the surgeon to fold the lens during insertion so that it can be made to pass through a very small slit, 2 to 4 mm in length, in the eye to gain access into the capsular bag.

The haptic part is still evolving however. The haptic structure needs to contact the interior of the anterior capsular sac essentially for 300 to 360 degrees to properly stretch the sac to anchor the replacement lens properly while minimizing rupturing or tearing of the bag. Some early haptic structures had two connections to the lens and formed two loops. An example of this structure is shown in U.S. Pat. No. 4,494,254 to Lopez.

Later haptic structures used only one connection to the lens. Examples of such structures may be seen in U.S. Pat. No. 4,842,600 to Feaster; U.S. Pat. No. 4,950,290 to Kamerling; U.S. Pat. No. 5,133,751 to Bayer; and U.S. Pat. No. 6,364,906 to Baikoff. These haptic structures have one end secured in the lens structure. The other haptic end has a single spiral that leads into an annular section that forms a ring. The known haptic structures, whether with one or two connections to the lens, are essentially coplanar with the lens. That is, when the intraocular lens was implanted correctly, the annular coil or ring portion of the embedded haptic touched the inside of the capsular sac through a 300 to 360 degree arc and the lens portion was substantially in the same horizontal plane as the haptic portion.

Some haptic structures, for example, U.S. Pat. No. 4,842,600 to Feaster, had an adjustment for the diameter of the annular part, which was accomplished by affixing the diameter with slide holes on the ends of the haptic structure. Some others used horizontal tensioning of the annular part to obtain the correct diameter for maintaining contact with the capsular bag. For example, U.S. Pat. No. 4,950,290 to Kamerling; U.S. Pat. No. 5,133,751 to Bayer; and U.S. Pat. No. 6,364,906 to Baikoff.

U.S. Pat. No. 5,653,752 describes a method for adjusting the curvature of the corneal using intrastromal corneal rings. This work is only marginally relevant to the present invention which uses the natural focusing mechanism of the eye to adjust the lens position relative to the retina and also influences the shape of the capsular sac.

The intraocular replacement lens discussed heretofore attempted to simultaneously place the lens and hold it in correct position while also giving horizontal geometric stabilization to the capsular bag. The known art however fails to provide a suitable replacement structure that retains the ability of the implant recipient to be able to focus on both close and far objects as a natural lens does or that stabilizes both the horizontal and vertical geometries of the capsular bag. Thus, most implant recipients require corrective devices to achieve normal vision.

Thus, a need exists for an improved intraocular lens implant structure that can be moved to accommodate focal length adjustments in a fashion similar to that of a natural lens to retain the ability to focus on objects at different distances from the observer. It is also desirable to provide an interocular lens that stabilizes the capsular bag in both the vertical and horizontal axes. It is still further desirable to provide such stabilization conically to mimic the natural shape of the capsular bag. An improved replacement lens would permit the recipient to use their eyes as before and more particularly would enable the recipient to flex the lens to properly focus images upon their retina.

SUMMARY OF THE INVENTION

In accordance with one exemplary embodiment of the present invention, an accommodative intraocular lens is provided that may be implanted to replace the eye's natural lens following a conventional surgery to remove the natural lens. The intraocular lens structure includes an optical portion and a haptic portion. The optical portion includes a replacement lens while the haptic portion includes the structure that holds the lens in position while keeping the anterior capsular sac or bag taunt and annular in shape.

A requirement for the haptic portion is that it must contact the interior of the capsular bag sufficiently to provide proper stretching to minimize the chances of rupturing the bag. The capsular bag is an ovate shaped body and as such has a three dimensional shape. The haptic in the present invention stabilizes not only the annular structure of the peripheral zone at the capsular sac's largest diameter but also stabilizes the conical structure of the capsular sac as well. Thus, stabilization is provided in both the horizontal and vertical axes. The structure of the haptic in the current invention is such to accomplish this. The structure may also provide peripheral support if formed with a parabolic cross-section.

In one exemplary embodiment, the haptic structure of the present invention aids in maintaining the exterior of the posterior portion of the capsular sac, i.e. that portion of the capsular sac anterior to the plane of its maximum diameter, in a parabolic cone. The haptic structure includes a helical coil of increasing radius from the lens to the terminating annular ring that thus forms a conical coil spring. This spring shape has characteristics that are responsive to the focusing muscles of the eye. The terminal end of the spring includes a bulbous enlargement that prevents the tip from injuring the capsular sac during insertion.

Thus, a principal object of the present invention to provide an intraocular replacement lens that is accommodative in that it can be focused in a manner similar to a natural eye lens.

Another object of the present invention is to provide a structure that prevents damage to the capsular sac during the implantation process.

Yet another object of the present invention to provide stabilization to the anterior portion of the capsular sac so that it maintains a natural shape.

Yet another object of the present invention is to provide a replacement lens that stabilizes the capsular bag in both the horizontal and vertical axes.

A related object of the present invention is to provide a replacement lens that stabilizes the capsular bag in both the horizontal and vertical axes while also providing peripheral support for the capsular bag.

Another object of the present invention is to provide a replacement lens that may be flexed like a natural lens.

An object of the present invention is to provide a replacement lens that has a biasing mechanism to permit lens relocation relative to the retina.

These and other objects and advantages of the present invention, along with features of novelty appurtenant thereto, will appear or become apparent in the course of the descriptive sections.

BRIEF DESCRIPTION OF THE SEVERAL VIEWS OF THE DRAWINGS

In the following drawings, which form a part of the specification and which are to be construed in conjunction therewith, and in which like reference numerals have been employed throughout wherever possible to indicate like parts in the various views:

FIG. 1 is a perspective view of an exemplary embodiment in accordance with the present invention;

FIG. 2 is an elevational view taken generally from the side thereof;

FIG. 3 is a top plan view thereof;

FIG. 4 is an environmental view taken generally from the side with portions removed or shown in section for clarity;

DETAILED DESCRIPTION OF THE INVENTION

Figure 5:
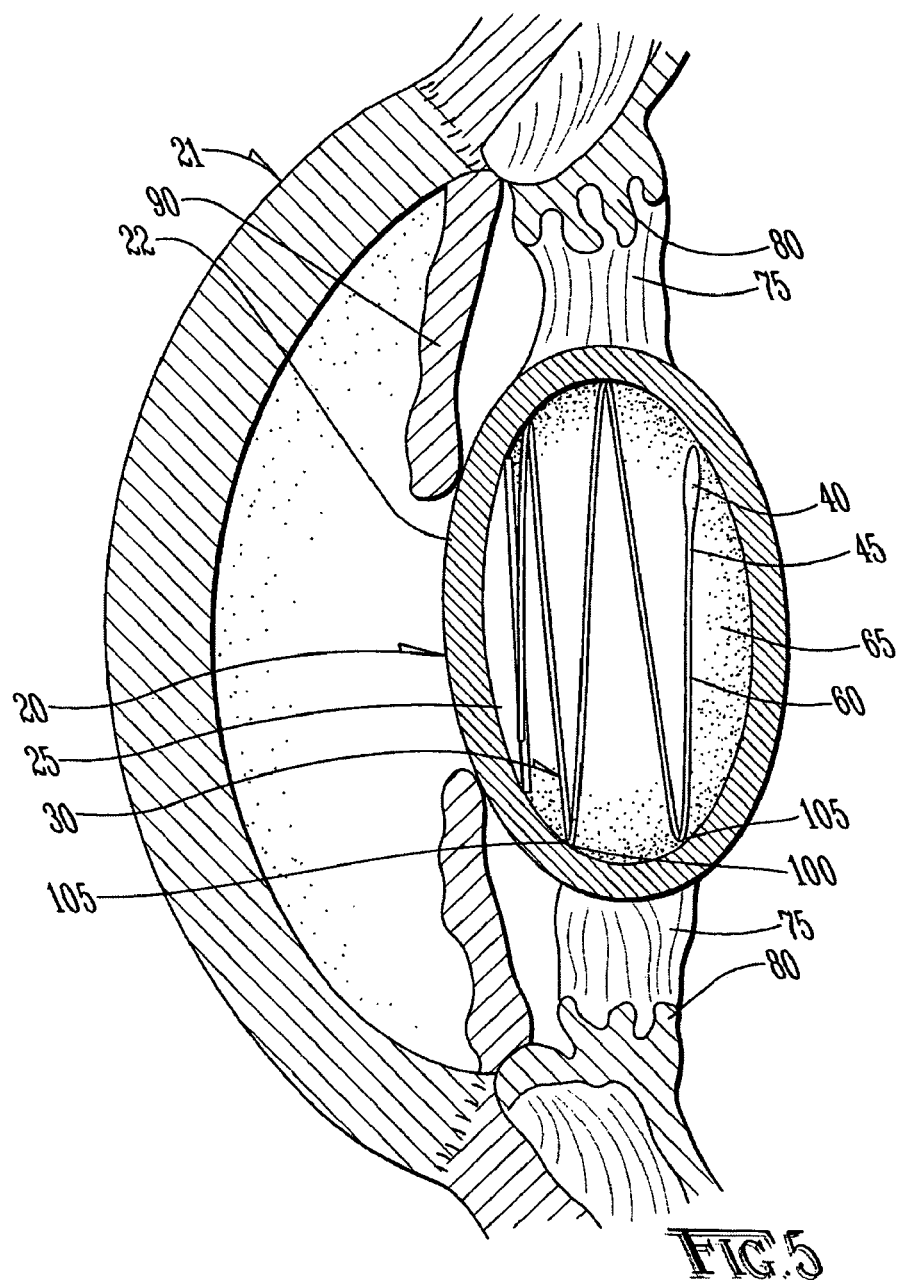
FIG. 5 is an enlarged view of the area designated by circle 5—5 in FIG. 4 thereof and we present eye and lens in accommodative state with the lens moved forward.

An exemplary embodiment in accordance with the present invention is generally referred to as replacement accommodative intraocular lens. The lens is generally designated by reference numeral 20 in FIGS. 1–8. The accommodative intraocular lens consists of two primary parts, the lens or optical portion 25 and the haptic portion 30 that holds the optical lens 25 in the correct position relative to the eye, both the radial and the elongated symmetry of the eye. The replacement lens 20 is normally inserted into the capsular bag 22 as will be discussed hereinafter.

The lens structure 25 can be made of polymethylmethacrylate (PMMA), silicone, or acrylic, all of which are biocompatible with human physiology and known to those skilled in the art. The optical requirements for the lens are also established common knowledge to those skilled in the art. That is, the lens will meet certain dimensional requirements as well as sanitary requirements and the like.

The haptic structure 30 can also be made from PMMA, proline, or acrylic strands. All these materials are biocompatible as discussed hereinbefore. Other materials may also be utilized and are deemed within the scope of the invention. The thickness of the strand and its spring constant are as needed to simulate the compressibility of a natural lens. It has been found for example that a compressibility in the range of approximately one to ten pounds per square inch is acceptable.

The haptic structure 30 includes a proximate end 35. The proximate end 35 is secured to the side of the lens structure 25 at a slight angle to the plane of the lens 25 and may even be inserted therein. The angle is selected so that after implantation into the eye, the lens 25 will be positioned in a plane parallel to the plane of the haptic's terminal annular ring. In this position, the lens pushes against the inside of the capsular sac 22 with equal or nearly equal forces at all points of contact in a manner similar to the natural lens.

The haptic's anterior end 40 may have a bulbous shape or other shape to avoid rupture during insertion into the capsular bag 22.

The haptic structure 30 extending between the proximate point of attachment 35 and the terminal end 40 forms a thin cylindrical strand arranged in a substantially helical shape, i.e. a non-plane curve whose tangents are all equally inclined to a given plane. In this instance, the helical shape includes a plurality of coils 50 that get diametrically larger as one transverses from the point of embedment 35 to the terminal annular ring 45. Thus, each revolution made by the haptic may be referred to as a coil 50.

In one preferred embodiment, at least two coils are present although more may be utilized. The coil spacing 55 coupled with the haptic's natural resistance to deformation gives rise to a spring action between the anterior and the posterior of the device 20 when properly positioned in the capsular bag 22.

The spacing between individual coils 55 is best seen in FIG. 2. The parabolic outline 58 formed by (shown by the dashed line in FIG. 2) the exterior from the proximate end 35 to the anterior portion 40 of the accommodative intraocular lens 20 is shown as well. Thus, the entire lens structure 20 forms a conic support for the capsular bag 22. It is also readily apparent from FIG. 2 that the terminal portion of the annular ring 45 of the un-implanted accommodative intraocular lens 20) does lie in a separate plane that is parallel to the optical lens 25. This feature facilitates operation of the accommodative intraocular lens and will be discussed in detail in subsequent sections herein.

In one exemplary embodiment, the coil spacing extends vertically approximately 9 mm. While the lens may be of varying diameters, a diameter of 7 mm has been suitable in many instances. Of course, other dimensions are possible for both and are within the scope of the present invention.

In FIG. 3 the nature of the lateral spacing of the helix coils is readily apparent. The terminal coil 55 of the helix forms at least five sixths of an annular ring that lies in a plane parallel to the plane of the lens 25. The terminal annular ring as used herein denotes a circular structure that completes an arc of circa of approximately 300 degrees and has a gap of circa 60 degrees so that it may contract or expand horizontally after it is implanted.

An exemplary general environmental embodiment of the accommodative intraocular lens is shown in FIG. 4. Of particular note is the location of the optics in the anterior portion of the eye. The focal length is the distance from the lens 25 and the retina 70. It should be understood that the eye is naturally focused by changing the focal length and/or the curvature of the natural lens. The portion of the eye where the accommodative intraocular lens will be located is shown in greater detail in FIGS. 5 and 6.

When the accommodative intraocular lens 20 is implanted in the eye as seen in FIG. 5, the terminal ring 60 will fit into the portion of the capsular sac 22 with the largest diameter, and will be stabilized there as to move in the posterior direction will cause the terminal ring 60 to contract. This contraction is resisted by the spring action of the haptic's terminal annular ring 60 to being compressed into a ring of smaller diameter. Movement in the anterior direction is resisted by this same force as well as that arising from the spring action of the spring formed by the helix 30, which also keeps the lens 25 firmly positioned correctly in the center of the anterior portion of the capsular sac 22. This spring action of the helix is selected such that it is responsive to the magnitude of force produced by the natural focusing muscles of the eye, which are the lens zonules 75 in combination with the ciliary bodies 80. The different spring actions are obtained by using increasing diameters of the strands that compose the haptic 30.

Figure 6:
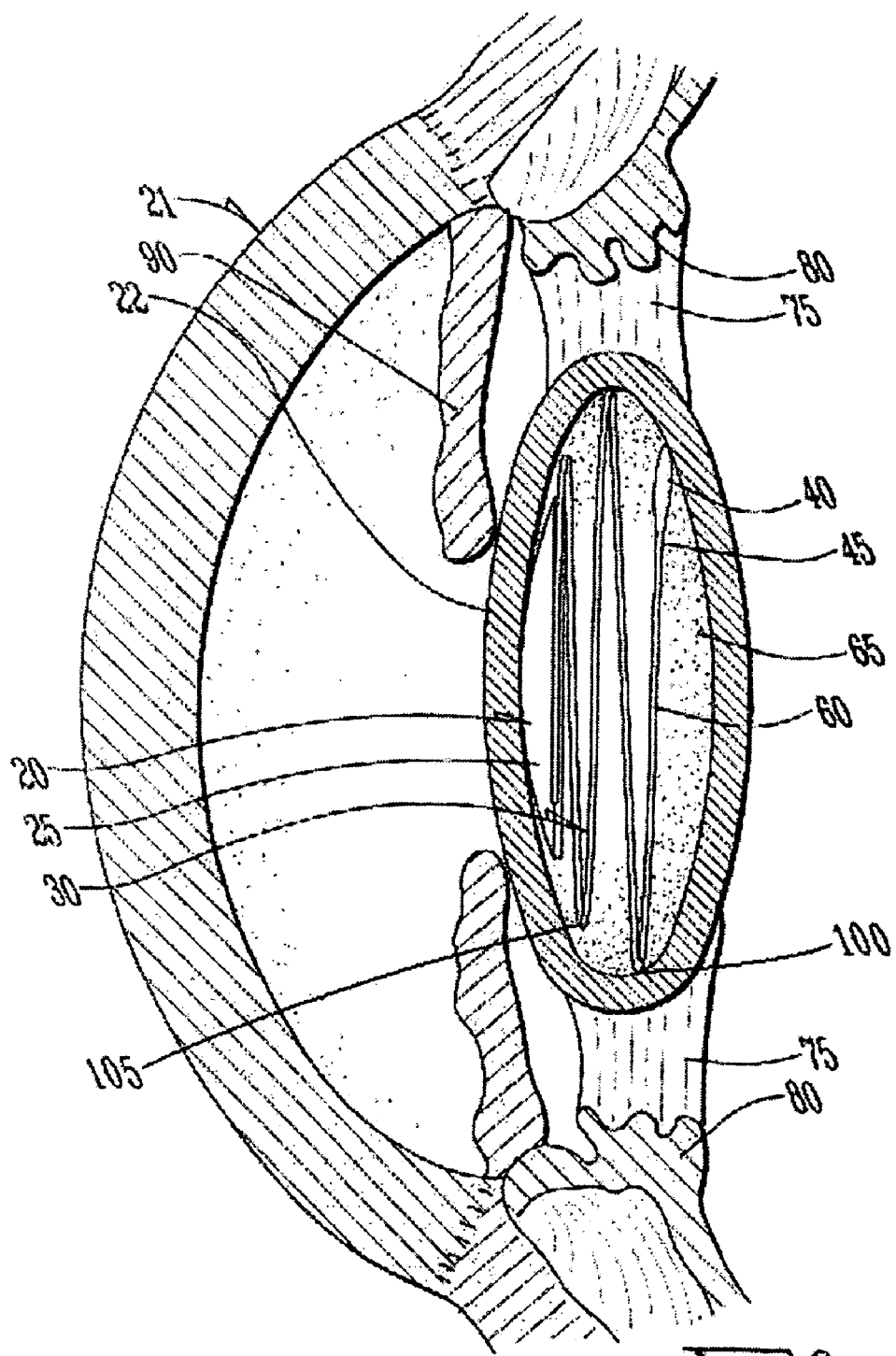
FIG. 6 is an enlarged view of the area designated by circle 5—5 in FIG. 4 but showing its position and appearance in the nonaccomodative state.

The accommodative intraocular lens adjusts focal length by moving from a non-accommodative state to an accommodative state. The non-accommodative state occurs when the ciliary bodies 80 are relaxed which maximally tightens the zonules 75 and applies tension to the capsular sac 65 as is shown in FIG. 6. While in non-accommodative state, the capsular sac 65 is stretched thin and the coil spring of the haptic 30 is compressed.

In the accommodative state as shown in FIG. 5, the ciliary bodies 80 are contracted, thereby loosening the zonules 75 which lessen the tension on the capsular sac 65. As the tension is removed, the haptic's spring properties cause it to distend and push the lens more anterior. This anterior lens motion effectively increases the power of the lens allowing the implantee to focus on near objects. The spring qualities will thus effectively emulate the natural lens's characteristics in regard to compression and distention and move the lens posteriorly and anteriorly.

Figure 7:
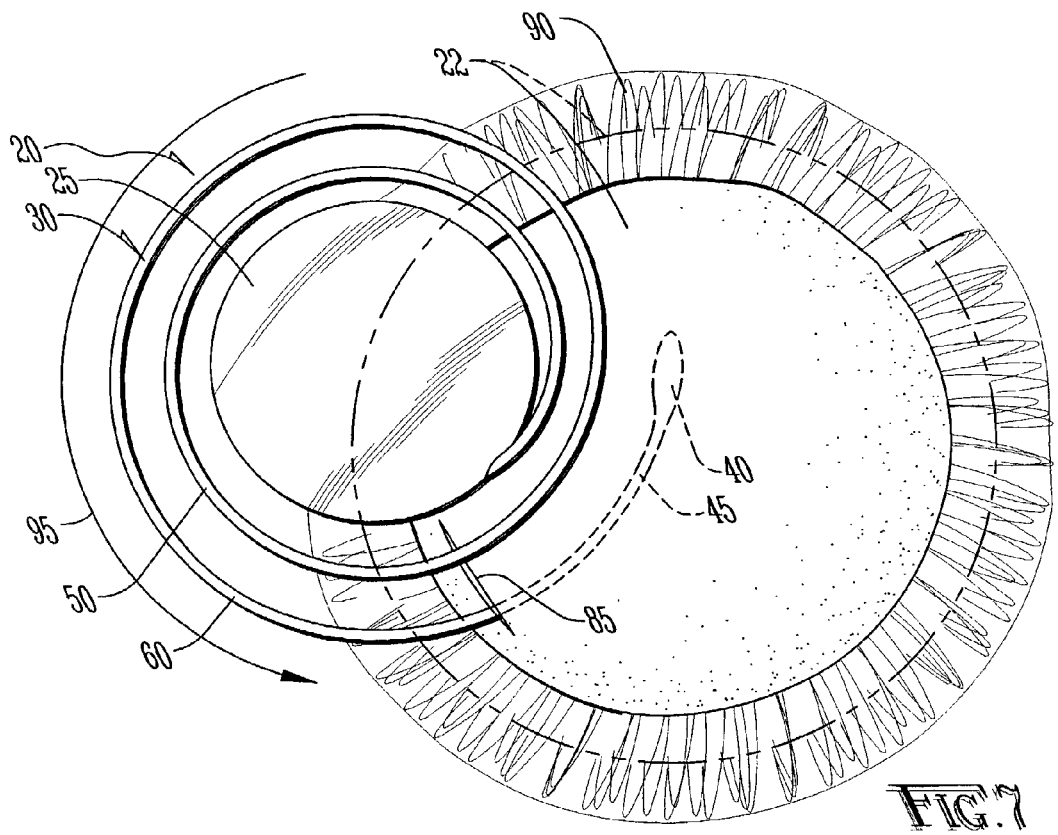
FIG. 7 is a top plan view with portions removed or shown in section for clarity and illustrating the partial insertion of the intraocular lens into an eye; and, FIG. 8 is a top plan view with portions removed or shown in section for clarity and illustrating the complete insertion of the intraocular lens into an eye.

To implant the accommodative intraocular lens, an incision 85 shown in FIG. 7 is made and the cataract removed in the usual manner. If capsulorrhexis is done during the cataract removal, the diameter of the circular tear to the anterior portion of the capsular sac should be slightly smaller than the lens diameter that is to be subsequently implanted. Note that the capsular sac 65 is behind the iris 90 and the dashed line depicts its largest diameter. The bulbous end 40 is inserted through the incision 85 and directed into the capsular sac 65. The accommodative intraocular lens 25 is then rotated as indicated by arrow 95 until the entire haptic 30 is within the capsular sac 65. The lens 25 should follow last. The lens 25 is inserted by folding it or by enlarging the incision 85 either action is done immediately prior to its insertion through the incision 85.

Figure 8:
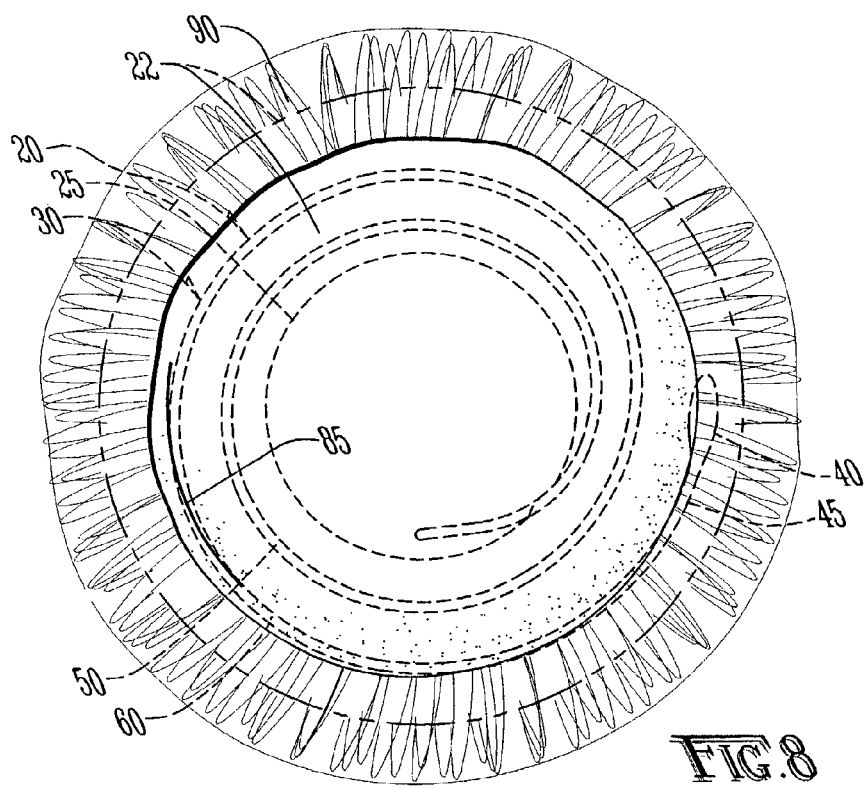

After the accommodative intraocular lens is inserted as shown in FIG. 8, its proper placement and alignment should be checked and adjusted as needed. The haptic's terminal ring 60 terminal ring should be at the largest diameter of the capsular sac 65. The lens 25 should be placed in the center of the pupil 95. If capsulorrhexis was done during the cataract removal, the circular tear to the anterior portion of the capsular sac should be positioned so that it is just over the edge of the implanted lens 25. The completion of the operation is in the normal and usual manner.

In one exemplary embodiment, the intraocular accommodative lens replaces at least a portion of a natural lens in the capsular bag of the eye. The lens is supported in the eye by a haptic structure that maintains a desirable shape in the capsular bag to subsequently facilitate focusing of the eye as would naturally occur when focusing and to thus maintain the accommodavite functionality of a fully functional normal eye. The haptic structure thus permits the eye to focus accommodatively to preserve or enhance the patient's sight.

The lens structure uses a biocompatible material such as polymethylmethacrylate, silicone and acrylic or the like.

The haptic structure extends, preferentially integrally, from the lens. The haptic structure includes a plurality of coils. The plurality of coils provide a biasing force. The biasing force moves the lens structure accommodatively both anteriorly and posteriorly in the eye.

The plurality of coils ideally form a conic structure. The conic structure maintains a desirable shape for the capsular bag. The haptic includes a plurality of substantially horizontally disposed peripheral surfaces 105 adapted to maintain outward pressure against the internal wall of the capsular bag to maintain its diametric and horizontal extent in a fashion to mimic a fully function and normal human bag. The haptic also includes a plurality of substantially vertically disposed peripheral surfaces 100 adapted to maintain outward pressure against the internal wall of the capsular bag to maintain its vertical extent in a fashion to mimic a fully function and normal human bag.

One type of advantageous conic the plurality of coils may assume is that of a parabilic helix. In a parabolic helix, the helix may be described as having a vertical parabolic cross-section. Thus, one axis of a cross-section may be said to lie in a vertical plane while another may be said to lie in a horizontal plane.

It is desirable for the base of the helix to be seated against an anterior portion of the bag adjacent the largest diameter of the anterior portion. In this fashion, the helix is seated rearwardly in the bag and adapted to bias the lens against the posterior portion of the eye in a desirable configuration.

In all described configurations of the present invention, the haptic moves the lens in response to natural eye movements to focus an object to be seen upon the retina of the eye while maintaining the desirable shape of the capsular bag.

It is interesting to also note that the lens may be placed in the capsular bag upside down and will still have its accommodative properties as previously described, though the lens power calculation constant will differ.

From the foregoing, it will be seen that this invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A replacement intraocular accommodative lens for spiral insertion into the capsular bag of a recipient's eye and adapted to move in response to natural eye movements to focus an object to be seen upon the retina of the eye, said accommodative lens comprising:
   an optic formed of biocompatible material;
   a conic haptic extending from said optic and adapted to be seated in the capsular bag, said conic haptic including a plurality of coils adapted to bias said lens against a posterior section of the capsular bag, said conic haptic including a bulbous terminus; and
   whereby said conic haptic forms a parabolic helix having a vertically oriented parabolic cross-section, said helix having a base adapted to be seated against an anterior portion of the bag and adapted to bias said lens against the posterior portion of the bag.

2. The lens as recited in claim 1 wherein said biocompatible material is chosen from the group including polymethylmethacrylate, silicone and acrylic.

3. The lens as recited in claim 1 wherein said conic haptic is adapted to be seated in the capsular bag adjacent the widest diameter of the bag.

4. The lens as recited in claim 3 wherein said conic haptic includes a plurality of substantially horizontally disposed peripheral surfaces adapted to maintain outward pressure against the internal wall of the capsular bag to maintain its horizontal extent.

5. The lens as recited in claim 4 wherein said plurality of substantially horizontally disposed peripheral surfaces are variably spaced vertically to form the exterior surface of a continuous wound coil.

6. The lens as recited in claim 3 wherein said conic haptic includes a plurality of substantially vertically disposed peripheral surfaces adapted to maintain outward pressure against the internal wall of the capsular bag to maintain its vertical extent.

7. The lens as recited in claim 6 wherein said plurality of substantially vertically disposed peripheral surfaces are variably spaced horizontally to form the upper surface of a continuous wound coil.

8. An intraocular accommodative lens adapted to replace at least a portion of a natural lens in the capsular bag of the eye, said accommodative lens being supported therein by a conic haptic adapted to maintain the ovate shape of the bag to facilitate focusing of the eye, said accommodative lens comprising:
   an optic of biocompatible material;
   said conic haptic extending from said optic, said conic haptic adapted to be seated in the capsular bag and including a plurality of coils adapted to provide a biasing force to move said lens anteriorly and posteriorly in the eye and wherein said plurality of coils form a parabolic helix having a vertical parabolic cross-section, said helix having a base adapted to be seated against an anterior portion of the bag adjacent the largest diameter of the ovate shape of the anterior portion of the capsular bag and adapted to bias said lens against the posterior portion of the capsular bag;
   said conic haptic further including a bulbous terminus to facilitate insertion into the eye; and,
   whereby said conic haptic moves said lens in response to natural eye movements to focus an object to be seen upon the retina of the eye while maintaining the ovate shape of the capsular bag.

9. The lens as recited in claim 8 wherein said biocompatible material is chosen from the group including polymethylmethacrylate, silicone and acrylic.

10. The lens as recited in claim 9 wherein said conic haptic includes a plurality of substantially horizontally disposed peripheral surfaces adapted to maintain outward pressure against the internal wall of the capsular bag to maintain its horizontal extent and said conic haptic includes a plurality of substantially vertically disposed peripheral surfaces adapted to maintain outward pressure against the internal wall of the capsular bag to maintain its vertical extent.

11. An intraocular accommodative lens adapted to replace at least a portion of a natural lens in the capsular bas of the eye, said accommodative lens being supported therein by a conic haptic adapted to maintain the ovate shape of the bag to facilitate focusing of the eye, said accommodative lens comprising:
   an optic of biocompatible material;
   said conic haptic extending from said optic, said conic haptic adapted to be seated in the capsular bag adjacent the largest diameter of the ovate shape, said conic haptic including a plurality of coils adapted to provide a biasing force to move said lens anteriorly and posteriorly in the eye and wherein said plurality of coils form a parabolic helix having a vertical parabolic cross-section, said helix having a base adapted to be seated against an anterior portion of the bag adjacent the largest diameter of the ovate shape of the anterior portion and adapted to bias said lens against the posterior portion of the capsular bag;
   said conic haptic further including a bulbous terminus to facilitate insertion into the eye; and,
   whereby said conic haptic moves said lens in response to natural eye movements to focus an object to be seen upon the retina of the eye while maintaining the ovate shape of the capsular bag.

12. The lens as recited in claim 11 wherein said biocompatible material is chosen from the group including polymethylmethacrylate, silicone and acrylic.

13. The lens as recited in claim 11 wherein said conic haptic includes a plurality of substantially horizontally disposed peripheral surfaces adapted to maintain outward pressure against the internal wall of the capsular bag to maintain its horizontal extent and said conic haptic includes a plurality of substantially vertically disposed peripheral surfaces adapted to maintain outward pressure against the internal wall of the capsular bag to maintain its vertical extent.

* * * * *